United States Patent [19]

Seeley et al.

[11] 4,132,226

[45] Jan. 2, 1979

[54] BIOPOTENTIAL MOVEMENT ARTIFACT INHIBITING SYSTEM

[75] Inventors: Robert L. Seeley; William F. Flanigan, both of San Diego, Calif.

[73] Assignee: The United States of America as represented by the Secretary of the Navy, Washington, D.C.

[21] Appl. No.: 815,327

[22] Filed: Jul. 13, 1977

[51] Int. Cl.² ............................................. A61B 5/04
[52] U.S. Cl. ............................. 128/2.1 R; 128/2.1 B; 360/7; 346/33 ME
[58] Field of Search ................ 128/2 N, 2 V, 2.05 A, 128/2.05 R, 2.05 T, 2.06 A, 2.06 B, 2.1 B, 2.1 M, 2.1 R, 2.05 M; 346/33 M, 33 MC, 33 ME; 360/87, 69, 75

[56] References Cited

U.S. PATENT DOCUMENTS

| | | | |
|---|---|---|---|
| 2,380,392 | 7/1945 | Begun | 360/7 |
| 3,181,171 | 4/1965 | Erickson | 346/33 M |
| 3,185,925 | 5/1965 | Grass | 128/2.1 B |
| 3,401,395 | 9/1968 | Neher | 346/33 |
| 3,478,328 | 11/1969 | Schillinger | 128/2.1 B |
| 3,587,564 | 6/1971 | Hagan | 128/2.06 R |
| 3,843,838 | 10/1974 | Wanek | 360/69 |
| 3,885,090 | 5/1975 | Rosenbaum | 360/7 |

FOREIGN PATENT DOCUMENTS 1293306  10/1972  United Kingdom ....................... 360/69

OTHER PUBLICATIONS

Debecker, J. et al., "Automatic Suppression of Eye Movement and Muscle Artifacts When Averaging Tape Recoded Cerebral Evoked Potentials", EEG and Clin Neurophys.

Roby, R. E. et al., "A Simplified Circuit for Stimulus Artifact Supression," Hrnl. of EEG and Clin. Neurophys. vol. 39 No. 1 pp. 85–87, Jul. 1975.

Primary Examiner—Robert W. Michell
Assistant Examiner—Francis J. Jaworski
Attorney, Agent, or Firm—Richard S. Sciascia; Ervin F. Johnston; Thomas Glenn Keough

[57] ABSTRACT

The broadband auditory thresholds of marine mammals are determined by an apparatus which compensates for the animals' movement artifact. A number of evoked responses to audio stimuli are average during discrete time intervals. This approach reduces the effects of potentials attributed to movements of the animal, for example, the opening and closing of the blow hole. A threshold detector circuit, a tape delay and related circuitry electronically cooperate to block potentials attributed to the movement artifact when the potentials exceed the likely magnitude of the evoked response. Optionally, an oscilloscope is used to provide a visual representation of the evoked response and the potentials are manually inhibited when the movement artifact masks or otherwise overrides the evoked response.

10 Claims, 5 Drawing Figures ated to the movement artifact and to pass on to a signal

BIOPOTENTIAL MOVEMENT ARTIFACT INHIBITING SYSTEM

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

Marine mammals and, particularly, cetaceans have long been a source of great interest. Their uncanny ability to navigate and feed under conditions of near zero visibility is due to the fact that they "see" acoustically. In order to determine what frequencies or groups of frequencies contribute to the animals' high resolution, the auditory thresholds at discrete frequencies within the spectrum of the projected and reflected signals should be known. This can be determined after an animal is safely secured and kept moist to avoid injury. Electroencephlograph (EEG) electrodes are properly placed and acoustic energy at discrete frequencies within an expected frequency range is projected toward the animal. Each time a frequency is projected and the animal hears it, a potential is involuntarily evoked. The potential is picked up by the EEG electrodes and fed to monitoring and recording circuitry. However, since the evoked potentials are minute in amplitude, in the range of less than $1.0 \times 10^{-5}$ volts, they are difficult to detect. Merely, making the equipment more sensitive is not the answer since much greater potentials are picked up by the EEG electrodes whenever the animal moves. This movement occurs as the animal shifts about on its padded stretcher, or, as is much more common that the potentials attributed to movement, the movement artifact, are caused by the animal's opening and closing its blow hole. Whenever the movement artifact is present, the monitoring equipment responds to the generated potentials and the potentials attributed to the evoked response are obscured. It is obvious, therefore, that during the time when the animal is shifting or its blow hole is opening and closing, evoked response potentials to an acoustic stimulus are compromised. Even if several responses to the same frequency of acoustic stimuli were averaged without any movement artifact present, the artifact present during another response, when averaged with the others, would greatly distort or override the accumulated responses for a particular frequency of interest. Therefore, there is a continuing need in the state-of-the-art for an apparatus capable of measuring the auditory thresholds of marine mammals by recording the evoked potentials of auditory stimuli which is not compromised by the potentials atributed to the movement artifact.

SUMMARY OF THE INVENTION

The present invention is directed to providing an apparatus for differentiating the evoked analog potentials representative of evoked responses to audio stimuli by a marine mammal from the movement analog signals representative of the movement artifact. A tape recorder is coupled to receive all of the analog potentials of the marine mammal for storing them a predetermined time. An automatic threshold detector circuit is coupled to receive all of the analog potentials for generating inhibit signals when the magnitudes of the analog potentials exceed a predetermined threshold. A delay circuit is coupled to the threshold detector to delay the inhibit signals a period substantially equal to the predetermined storage time of the tape recorder. An inhibiting circuit is connected to the tape recorder and to the delay circuit for inhibiting the transmission of the stored potentials from the recorder when the inhibit signals indicate that the analog potentials include the potential attributed to the movement artifact and to pass on to a signal averager the analog potentials when they are representative of the evoked response.

OBJECTS OF THE INVENTION

It is an object of the invention to provide a means for measuring the auditory threshold of marine mammals.

Yet another object of the invention is to provide a means for reducing the effects of the movement artifact with respect to the evoked response.

Yet another object is to provide for signal averaging of an evoked response to audio stimuli.

Yet another object is to provide an apparatus which reduces the influence of the movement artifact upon the determination of the evoked response in marine mammals.

Still another object of the invention is to provide an apparatus having an automatic threshold detector for inhibiting the averaging of analog potentials which are added to potentials attributed to the movement artifact.

Still another object is to provide an apparatus for determining the evoked response having the capability for visually monitoring the evoked response and to inhibit such response when the movement artifact is detected.

Yet another object is to provide an auditory threshold determining apparatus having a higher reliability due to the sequential triggering at discrete intervals of auditory stimuli and the monitoring of the evoked response immediately after triggering.

These and other objects of the invention will become more readily apparent from the ensuing description when taken with the drawings.

DESCRIPTION OF THE PREFERRED EMBODIMENT

Figure 1:
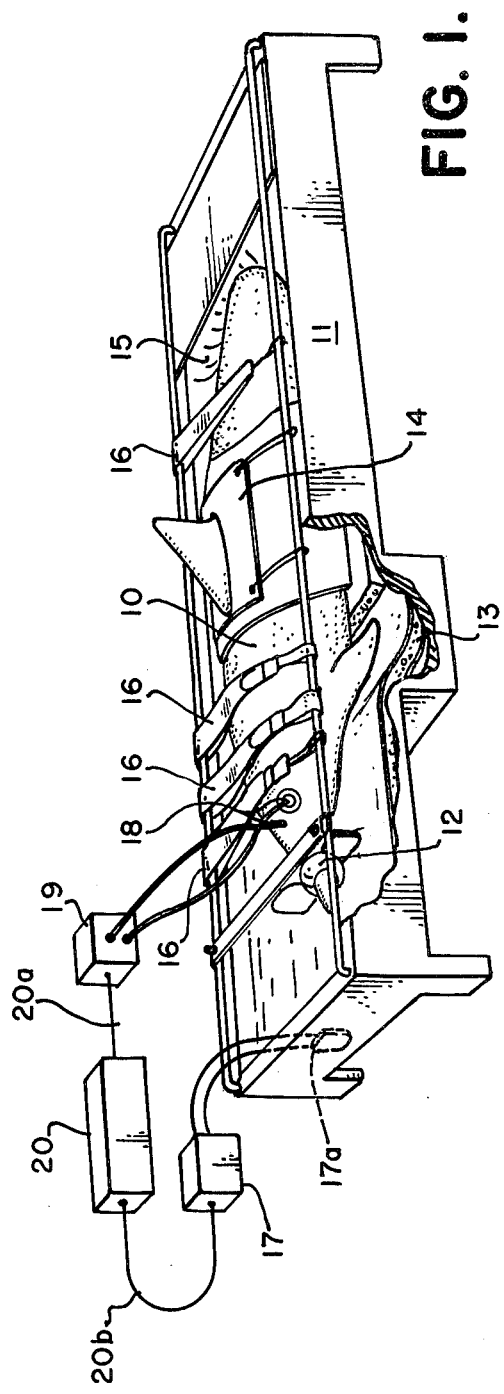
FIG. 1 is an isometric depiction of a marine mammal being given an audio test.

Referring now to FIG. 1 of the drawings, a cetacean 10 (a dolphin, porpoise, or small whale) is restrained in a testing tank 11. A nose pad 12, a pectoral fin pad 13, a dorsal saddle pad 14 and a tail pad 15 are provided to prevent injury of the animal while a number of overhead straps 16 retain it in the tank. The inside of the tank partially is filled with water and the unwetted, exposed dorsal surface of the animal is sprayed with water to prevent drying out and consequent injury.

Researchers have long been intrigued by the acoustic capabilities of cetaceans; all to one degree or another are capable of achieving a resolution heretofore unattainable by the finest sonars available to man. It is no wonder, then, that researchers strive to duplicate the animals' unique capabilities to aid in the fabrication of units to perform a variety of seismic and military tasks. First, however, designers need be aware of the animals' acoustic response or auditory thresholds over their working acoustic spectrum.

One way of determining the response is to ensonify the animal at discrete frequencies and magnitudes and to note its evoked potentials via EEG methods. Thus, discrete frequencies are generated at a frequency-trigger generator 17. The trigger-generator functions as a stimulator since its generated frequencies and trigger pulses stimulate the animal for the evoked response while the trigger pulses expedite a determination of the movement artifact. The generated frequencies are projected upon a test animal by transducer 17a. The transducer is separated from the animal a distance of approximately one meter although this separation is variable as the situation allows.

A pair of EEG electrodes 18 is properly located to assure detection of the involuntarily evoked potentials when the animal hears them. It has been found that some cetaceans hear better than others so that the evoked responses vary from animal to animal. One old animal had a very poor frequency response much the same as some humans have in their advancing years. In any event the evoked potentials are fed to a preamplifier stage 19.

From the preamplifier stage the signals are coupled to the inhibition system 20 via a lead 20a. Trigger pulses from frequency-trigger generator 17 are fed to the inhibition system via a lead 20b. The frequency of the trigger pulses is constant irrespective of the changing frequencies which drive transducer 17a. Elaboration on the circuitry forming the generator is dispensed with to avoid belaboring the obvious.

Even with the animal restrained as depicted, there can be a significant movement artifact which generates electric potentials. That is, potentials are generated across electrodes 18 as a result of movement by the cetacean. These movement artifacts are substantial when compared to the relatively minute amplitudes of the evoked potentials (in the range of approximately $1.0 \times 10^{-5}$ volts). While the restraining arrangement depicted is somewhat effective, the movement artifact attributed to the animals shifting its head, opening its mouth or breathing through its blow hole is sufficient to mask or otherwise override the evoked potentials created when the animal responds to impinging acoustic energy. Thus, the inhibition system 20 was developed to reduce the otherwise erroneous readings attributed to the movement artifact.

Figure 2:
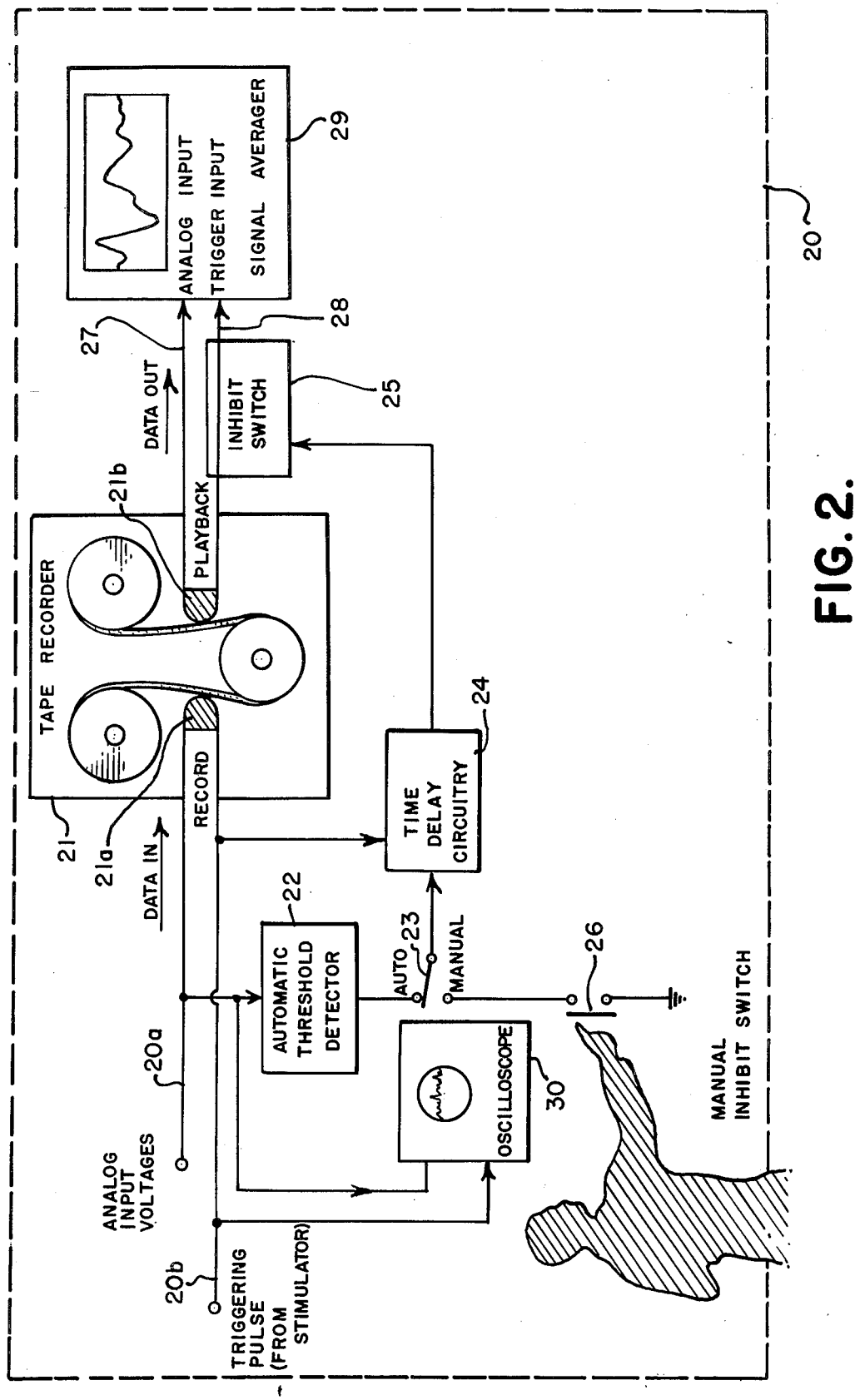
FIG. 2 is a block diagram of the principal constituents of this invention.
Figure 3A:
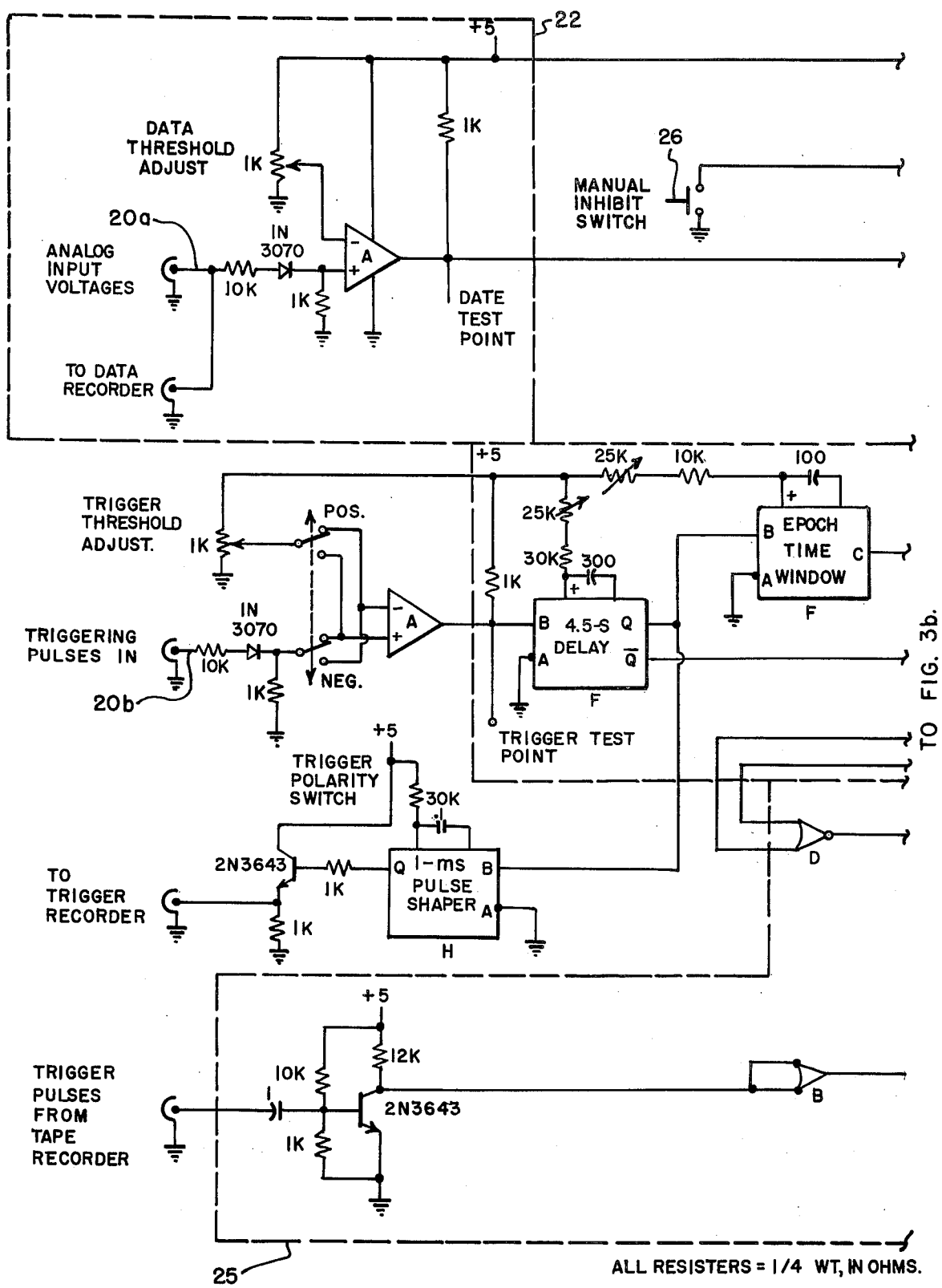
FIG. 3a and 3b are schematical representations of a portion of this invention.
Figure 3B:
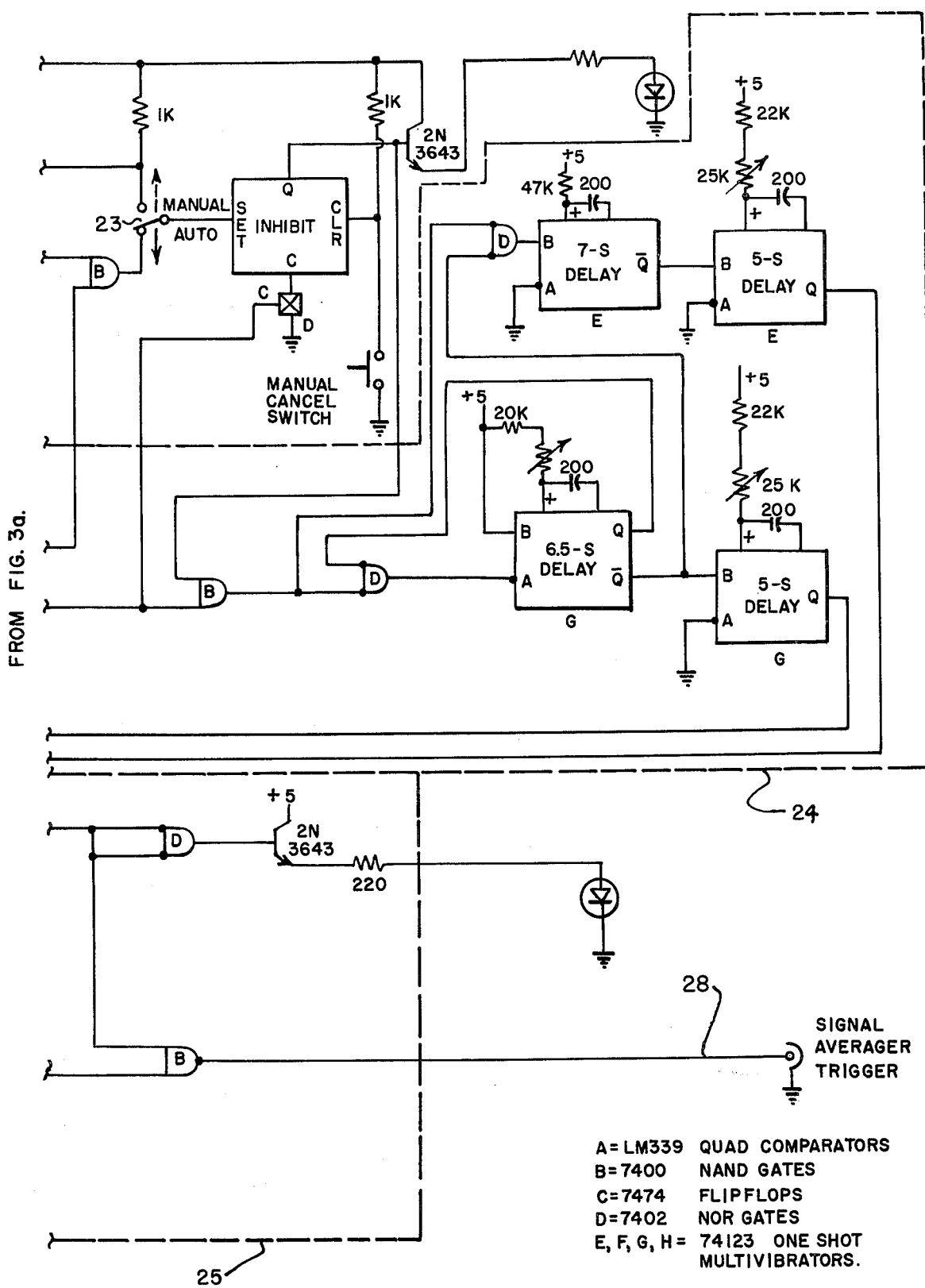

Referring to FIG. 2, the improved apparatus 20 is shown in block diagram form and in circuit diagram form in FIG. 3. Analog input voltages originating at the electrodes 18 reach the inhibition system via a lead 20a. At the same time, on lead 20b trigger pulses from the frequency-trigger generator 17 come into the system.

The analog input voltages are preferably attributed to the evoked response, however they may have components which are attributed to the movement artifact. In any event, the entire analog input voltages along with trigger pulses reach a tape recorder 21 and are recorded on a tape via a recording head 21a. The tape recorder selected is one of a number of commercially available varieties, here, a model 6100 Precision Instrument recorder was used. The recorder was run to give a delay of 13.5 seconds between the time data was recorded by record head 21a and it was reproduced by a playback head 21b.

The analog input voltages also were fed to an automatic threshold detector 22 which passed an inhibit signal when the composite analog input voltages exceeded a certain data threshold. This data threshold was preset to correspond to a potential less than a potential produced when a known movement artifact occurred but greater than the signal produced by an evoked response. When this threshold was exceeded, an inhibit signal was fed through a switch 23 when it was set in the automatic mode.

This inhibit signal reached time delay circuitry 24 which also responded to triggering pulses coming from the frequency-trigger generator 17. After a preestablished time, generally substantially the same time as the delay between recording and reproduction of the analog input voltages by a tape recorder, a signal is fed to an inhibit switch 25. If the preestablished threshold in detector 22 is exceeded, the inhibit switch blocks the passage of the trigger pulses from being fed via a lead 28 to a signal averager 29. The signal averager, a model 570 by Northern Scientific, averages several evoked response potentials and displays them on a X-Y recorder when trigger pulses arrive on lead 28 simultaneously with evoked responses arriving on lead 27.

Provision is also made for visually observing the analog input voltages. Switch 23 is snapped to the manual mode and a manual inhibit switch 26 is closed whenever the movement artifact is apparent on an oscilloscope 30. Closing the manual inhibit switch causes the inhibit switch 25 to prevent the trigger pulses from reaching the signal averager and effectively disregards the data appearing on output lead 27.

Looking now to FIGS. 2, 3a, 3b and 4, tape recorder 21 stores analog input voltages appearing on lead 20a for 13.5 seconds, that being the time needed for the magnetic tape to travel between record head 21a and playback head 21b. The threshold detector 22 and the time delay circuitry 24 were designed on the basis of the interstimulus interval, the EEG epoch time and the tape record/reproduce delay time (those being 5.0 seconds, 1.0 seconds, and 13.5 seconds, respectively).

Automatic movement artifact inhibition is accomplished by comparing the analog input voltages appearing on lead 20a to a preset data threshold voltage in the detector 22. If the analog input voltages exceed the preset data threshold voltage during the epoch time window, that being 0.5 seconds while sound is being projected to the animal, see FIG. 4, the inhibit flip-flop is automatically set and a movement artifact light emitting diode is energized. A 4.5 second delay interval follows the 0.5 period. At the end of the 4.5 second delay the inhibit flip-flop is cleared and the decision to inhibit is retained by initiating yet another time delay of 6.5 seconds or (if the 6.5 second delay was activated) 7.0 seconds.

Termination of either the 6.5 or 7.0 second delay begins an additional five second period during which triggering pulses reproduced at the playback head 21b are prevented from reaching signal averager 29, by the inhibit switch 25. A trigger inhibit light emitting diode indicates when inhibition occurs.

When the system is operated manually, triggering pulses initiate a one second display of the analog input voltages on an oscilloscope 30. The operator has 4.5 seconds from stimulus onset to decide whether to prevent inclusion of the EEG epoch in the accumulating evoked response in the signal averager 29. If the input voltages visually are determined to include the movement artifact, the inhibit switch 26 is closed and the voltages are blocked from the averager.

If, however, after the inhibit switch has been actuated and it is desired to include it in the averaged evoked response the manual cancel switch is actuated. This reverses any decision to inhibit a signal during either automatic or manual operation, see FIG. 3b for the manual cancel switch. In this latest instance the manual cancel switch must be actuated within the 4.5 seconds following the beginning of the stimulus onset.

Figure 4:
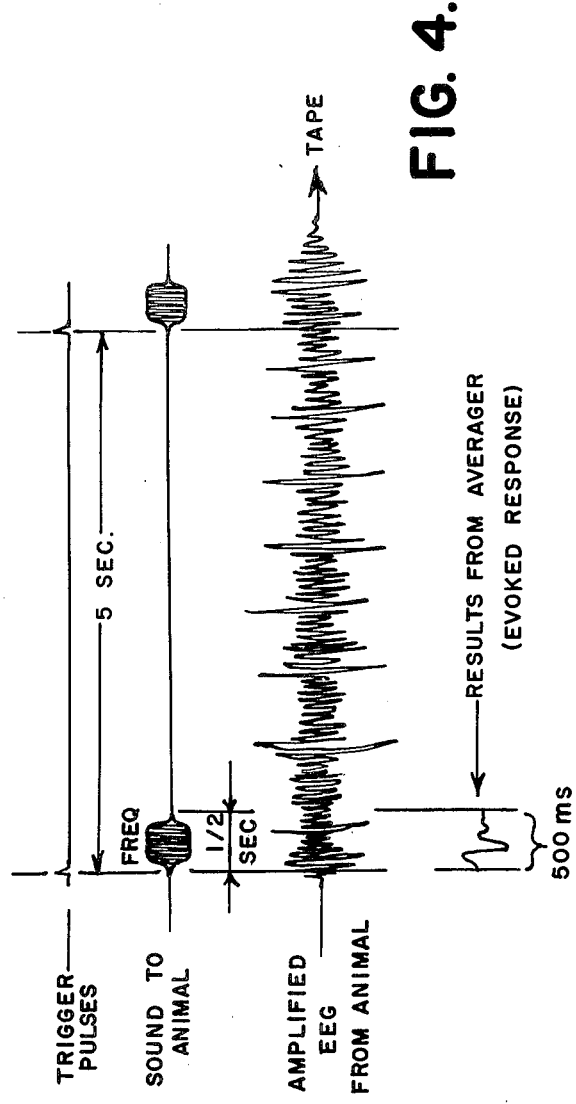
FIG. 4 depicts representative waveforms and time relationships.

Noting FIG. 4, the waveform depicted as being an amplified EEG from an animal is representative of typical analog input voltages appearing on lead 20a. It is apparent that it would be difficult to determine the evoked response in such a clutter, particularly when the extreme spikes, representative of the movement artifact, are included in the represented signal. It can be seen therefore that this invention, by sending an evoked response at discrete intervals and then comparing this sampled response in a threshold detector, greatly simplifies the task of deriving an evoked response from a composite waveform.

Tests were conducted ensonifying the animals from five to three hundred KHZ. Some of the test subjects showed "deafness" in certain frequency ranges. Training difficulties with the deaf animals might be directly correlated to their hearing loss.

Obviously, many modifications and variations of the present invention are possible in the light of the above teachings, and, it is therefore understood that within the scope of the disclosed inventive concept, the invention may be practiced otherwise than specifically described.

What is claimed is:

1. An apparatus for differentiating evoked analog potentials representative of evoked responses to audio stimuli by a marine mammal from movement analog potentials representative of the movement artifact comprising:

means coupled to receive all of the analog potentials from the marine mammal for storing them a predetermined time;

means coupled to receive all of the analog potentials for generating inhibit signals when their magnitudes exceed a predetermined threshold;

means coupled to the generating means for delaying the inhibit signals a period equal to the predetermined time of the storing means;

means connected to the delaying means and to the storage means and operative on the playback output of the storage means for inhibiting the transmission of the stored potentials upon the receipt of inhibit signals, the transmission inhibiting means being automatically actuated upon the receipt of the inhibit signals from the delaying means.

2. An apparatus according to claim 1 comprising:
   means connected to the storing means and inhibiting means for averaging potentials representative of evoked responses when the evoked analog signals are within the predetermined threshold in the generating means.

3. An apparatus according to claim 2 comprising:
   means carried on the marine mammal for sensing the analog potentials which are attributed to the evoked response and, alternatively, the evoked response and the movement artifact.

4. An apparatus according to claim 3 comprising:
   means for ensonifying the marine mammal with the audio stimuli at predetermined intervals.

5. An apparatus according to claim 4 comprising:
   means coupled to the ensonifying means, storing means and delaying means for triggering the differentiating of the evoked responses from the movement artifact during discrete time intervals separated by longer delay periods.

6. An apparatus according to claim 5 comprising:
   means coupled to receive the evoked analog potentials and movement analog potentials for providing a visual representation thereof.

7. An apparatus according to claim 6 comprising:
   means connected to the generating means and the delaying means for manually inhibiting the transmission of the stored potentials to the averaging means when the visual representation of the evoked analog potentials and movement analog potentials on the providing means exceeds a predetermined magnitude.

8. An apparatus according to claim 7 in which trigger pulses from the triggering means are stored on the storing means along with all the analog potentials and the inhibiting means prevents the trigger pulses from reaching the averaging means when the threshold magnitude is exceeded in the generating means to thereby block the transmission of the stored potentials from the averaging means.

9. An apparatus according to claim 8 in which the storing means is a magnetic tape having a playback head located following a record head to effect a delay equal to the predetermined time.

10. An apparatus according to claim 9 in which the ensonifying means is a projector of acoustic energy driven from 5 KHZ to 300 KHZ.

* * * * *